United States Patent
Morard et al.

(10) Patent No.: US 9,916,651 B2
(45) Date of Patent: Mar. 13, 2018

(54) METHOD FOR CHARACTERIZING A PART MADE OF A WOVEN COMPOSITE MATERIAL

(71) Applicant: SAFRAN, Paris (FR)

(72) Inventors: Vincent Morard, Versailles (FR); Estelle Parra, Fontenay le Vicomte (FR); David Tourais, Paris (FR)

(73) Assignee: SAFRAN, Paris (FR)

( * ) Notice: Subject to any disclaimer, the term of this patent is extended or adjusted under 35 U.S.C. 154(b) by 0 days.

(21) Appl. No.: 14/916,869

(22) PCT Filed: Aug. 29, 2014

(86) PCT No.: PCT/FR2014/052146
§ 371 (c)(1),
(2) Date: Mar. 4, 2016

(87) PCT Pub. No.: WO2015/033044
PCT Pub. Date: Mar. 12, 2015

(65) Prior Publication Data
US 2016/0203594 A1    Jul. 14, 2016

(30) Foreign Application Priority Data

Sep. 6, 2013    (FR) ...................................... 1358601

(51) Int. Cl.
| | |
|---|---|
| *G06T 7/00* | (2017.01) |
| *G01N 23/04* | (2018.01) |
| *G06K 9/46* | (2006.01) |
| *G06T 7/40* | (2017.01) |
| *F01D 5/28* | (2006.01) |

(52) U.S. Cl.
CPC ............ *G06T 7/0004* (2013.01); *F01D 5/282* (2013.01); *G01N 23/046* (2013.01); *G06K 9/46* (2013.01); *G06T 7/001* (2013.01); *G06T 7/40* (2013.01); *G06T 7/401* (2013.01); *F05D 2300/6034* (2013.01); *G01N 2223/615* (2013.01); *G06T 2200/04* (2013.01);
(Continued)

(58) Field of Classification Search
CPC ........................................ G06T 7/0004–7/001
See application file for complete search history.

(56) References Cited

FOREIGN PATENT DOCUMENTS

FR    2 357 680 A1    2/1978

OTHER PUBLICATIONS

Wald, Michael J., et al. "Spatial autocorrelation and mean intercept length analysis of trabecular bone anisotropy applied to in vivo magnetic resonance imaging." Medical physics 34.3 (2007): 1110-1120.*

(Continued)

*Primary Examiner* — Stephen R Koziol
*Assistant Examiner* — Raphael Schwartz
(74) *Attorney, Agent, or Firm* — Pillsbury Winthrop Shaw Pittman LLP

(57) ABSTRACT

A method of characterizing a part made of woven composite material, includes calculating autocorrelation values of a three-dimensional image in an observation window of the volume of the part for a plurality of spatial vectors used as the autocorrelation interval, and then detecting at least one local extremum in the autocorrelation value on a main orientation of the weaving in order to determine a mean in the observation window for the distance between neighboring parallel yarns.

8 Claims, 3 Drawing Sheets

(52) U.S. Cl.
CPC ........... *G06T 2207/10081* (2013.01); *G06T 2207/30124* (2013.01); *Y02T 50/672* (2013.01)

(56) References Cited

OTHER PUBLICATIONS

Kastner, Johann, "Advanced X-Ray Tomographic Methods for Quantitative Characterisation of Carbon Fibre Reinforced Polymers", NDT in Aerospace 2012.*
Toba, Eiji. "Determination of the Autocorrelation Function of Woven Fabrics Using Laser Speckle." Textile Research Journal 50.4 (1980): 238-244.*
Arithmetic mean, Wikipedia, the free encyclopedia, Jul. 16, 2012, https://en.wikipedia.org/w/index.php?title=Arithmetic_mean&oldid=502676378.*
Barrall, G. A., L. Frydman, and G. C. Chingas. "NMR diffraction and spatial statistics of stationary systems." Science 255.5045 (1992): 714.*
International Preliminary Report on Patentability and the Written Opinion of the International Searching Authority as issued in International Patent Application No. PCT/FR2014/052146, dated Mar. 8, 2016.
International Search Report as issued in International Patent Application No. PCT/FR2014/052146, dated Oct. 23, 2014.
Archer, E., et al., "Internal strain measurement and impact response of three-dimensional angle interlock woven carbon fibre composites," Journal of Reinforced Plastics and Composites, vol. 32, No. 12, Feb. 2013, pp. 912-924.
Crostack, H.-A., et al., "3D Analysis of MMC microstructure and deformation by μCT and FE simulations," Proceedings of SPIE, vol. 7078, Aug. 2008, 12 pages.
Hufenbach, W., et al., "A test device for damage characterisation of composites based on in situ computed tomography," Composites Science and Technology 72 (2012), pp. 1361-1367.
Heilbronner, R.P., "The autocorrelation function: an image processing tool for fabric analysis," Tectonophysics, vol. 212, No. 3-4, Oct. 1992, pp. 351-370.
Scott, A.E., et al. "In situ fibre fracture measurement in carbon-epoxy laminates using high resolution computed tomography," Composites Science and Technology 71 (2011), pp. 1471-1477.

* cited by examiner

METHOD FOR CHARACTERIZING A PART MADE OF A WOVEN COMPOSITE MATERIAL

CROSS-REFERENCE TO RELATED APPLICATIONS

This application is the U.S. National Stage of PCT/FR2014/052146, filed Aug. 29, 2014, which in turn claims priority to French patent application number 1358601, filed Sep. 6, 2013. The content of these applications are incorporated herein by reference in their entireties.

TECHNICAL CONTEXT

The invention lies in the field of methods of characterizing materials and structures, and in particular parts for mechanical engineering industries made of composite material having woven fiber reinforcement. Such parts are being used increasingly in the field of aviation because of their robustness and their low weight compared with parts made of other materials. These parts are also easy to fabricate. Among the parts concerned, engine parts are concerned in particular, including blades or casings for gas turbines. Because of the peculiar structure of such parts, where fiber reinforcement is embedded within a matrix, there exists a need to be able to inspect the characteristics of the woven fiber reinforcement at any time during the industrial production process or while the part in question is in use. This makes it possible to discover the level of fatigue or wear in the part and to identify defects or damage, if any. Naturally, since the woven reinforcement is embedded in the matrix, it is difficult to access it, and known methods are generally destructive, which is not satisfactory in a context of producing and using such parts in large numbers. It is therefore desirable to have methods of characterizing the fiber reinforcement that are not destructive.

X-ray tomography (axial tomography computed by a computer or CT-scanning) is a known method of performing non-destructive inspection of the inside of an article. It consists in acting in a plurality of planes to measure the attenuation imparted by the material to a beam of X-rays. A three-dimensional image is then reconstructed from the data picked up in each plane. Thereafter, it is possible to make sections of the 3D image in order to visualize the structure of the material in each section plane.

When applied to composite material having woven reinforcement, an approach as described above is hardly practical or would give rise to few satisfactory results. The woven reinforcement comprises an article of large size, having a multitude of warp yarns that are parallel to one another and of weft yarns that are likewise parallel to one another, these two sets of parallel yarns defining main orientations or characteristics directions of the weaving. The mean distance between the columns of warp yarns and the mean distance between the columns of weft yarns (distances between warp yarns and distances between weft yarns, or inter-warp distances and inter-weft distances) constitute information suitable for characterizing the reinforcement correctly in a zone where the weaving is uniform. However determining such information on the basis of a two-dimensional section of a 3D image, or on the basis of a plurality of such sections involves work that is tedious and difficult to automate. In order to carry it out well, it is necessary to identify the layers of weft yarns and the layers of warp yarns and to deduce therefrom their respective spacings. Any such measurement involves subjectivity on the part of the operator, and can be disturbed by all kinds of noise in the image. Furthermore, depending on the shape of the part under investigation, the section to be investigated can be difficult to identify, and it is also necessary to investigate a plurality of sections in order to obtain results that are reliable. Industrializing such a process is therefore not easy, and possibly even impossible, to implement.

DEFINITION OF THE INVENTION AND ASSOCIATED ADVANTAGES

In order to solve that difficulty and propose a non-destructive method that is easily automated and that provides reliable results, there is provided a method of characterizing a part made of woven composite material, the method comprising calculating autocorrelation values of a three-dimensional image of the volume of the part as acquired in an observation window for a plurality of spatial vectors used as the autocorrelation interval, and then in detecting at least one local extremum in the autocorrelation value on a main orientation (characteristic direction) of the weaving in order to determine a mean in the observation window for the distance between neighboring parallel yarns.

One property of autocorrelation is to obtain a unique global maximum that is obtained for the null vector. For vectors that are parallel to the characteristic directions of the weaving, it also has local maxima, which follow one another along a straight line in vector space parallel to the characteristic direction in question. These maxima can be visualized in the form of lobes in sections of vector space. By detecting at least one of these local maxima (or a minimum between two consecutive maxima), it is possible by reference to its distance from the null vector to obtain a multiple of the distance between neighboring parallel yarns. If the local maximum closest to the null vector has been detected, then this gives direct access to the distance between neighboring parallel yarns.

By using autocorrelation, the method eliminates the subjectivity that arises when an operator visually reads images of the volume of the part. Consequently, the method is more accurate and more reliable. That is why the method is also not very sensitive to noise. It makes it possible to measure the inter-warp and inter-weft distances throughout the part in non-destructive manner by making use of the three dimensions of the image of the volume of the part, whereas a human operator generally operates on two-dimensional sections of the image of the volume. Finally, it can be automated, and is thus faster than methods relying on reading by a human operator. In summary, it is both more accurate and easier to implement than techniques that do not use autocorrelation.

It is specified that the method applies to an image acquired by X-ray tomography or by any other technique for imaging the volume of a part. In particular, it should not be forgotten that X-rays are not essential, other tomography methods are known, and in particular nuclear magnetic resonance (NMR) tomography.

In a very advantageous implementation, the autocorrelation values are calculated by using the Wiener-Khinchin theorem, i.e. by using a mathematical function made up of direct and inverse Fourier transforms and of the modulus function for a complex number, and applying it to the three-dimensional image of the composite material part under investigation. That is a process that is simple, suitable for being automated, and that calculates continuously and exhaustively all of the autocorrelation function, thus making it possible to perform high quality investigation of the autocorrelation values that are grouped together in a three-dimensional "image" referred to as the "autocorrelation" image.

In a particular implementation, the method comprises detecting a characteristic direction of the weaving in the plurality of vectors, e.g. in the autocorrelation image. That involves identifying the alignment of local and global maxima corresponding to a weft-yarn or warp-yarn direction.

In an implementation, optionally combinable with the preceding implementation, the method comprises prior realignment of the 3D image of the composite material part in order to align the weaving axes (characteristic directions) with the axes of the image.

In order to characterize the part completely, the method may naturally provide for detecting extrema for the weft yarn direction and for the warp yarn direction in order to determine means in the observation window respectively for the distances between neighboring weft yarns and between neighboring warp yarns. Nevertheless, the method may be performed while paying attention only to the weft yarns or only to the warp yarns.

It is specified that in an implementation that is easy to perform, the extrema used are maxima and attention may be given in particular to extrema that are consecutive. The extrema used generally comprise the global maximum obtained for the null vector, but it is also possible to omit that by investigating two consecutive local extrema.

The method is particularly proposed for investigating a part made of three-dimensionally woven composite material and/or a part comprising carbon fibers in a carbon matrix. By way of example, the part may be a blade or a casing for an aeroengine.

Although the invention is centered on analyzing the image, the invention also provides a method that involves not only making use of the image but also acquiring it.

The description follows with reference to the accompanying figures.

LIST OF FIGURES

DETAILED DESCRIPTION OF AN IMPLEMENTATION OF THE INVENTION

Figure 1:
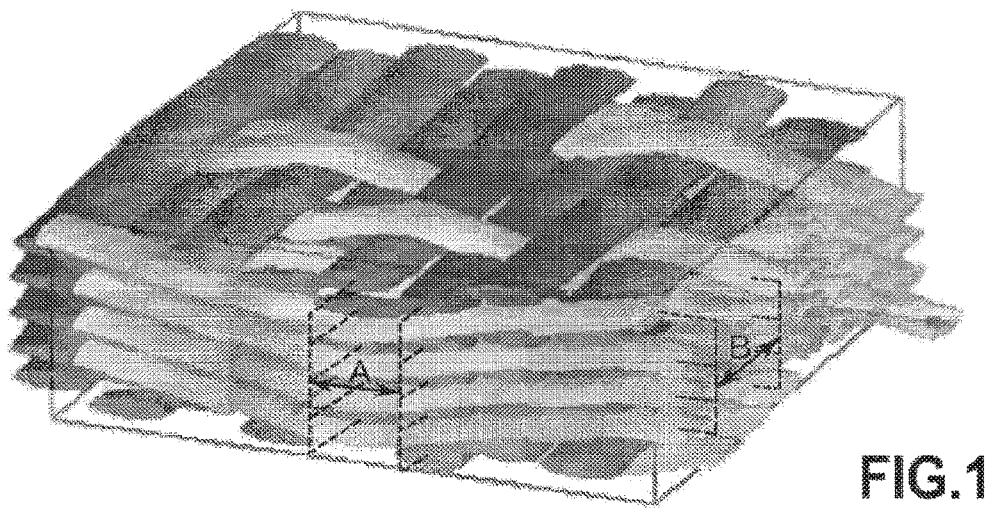
FIG. 1 is a diagram of 3D weaving used in a composite material part having woven fiber reinforcement.

The invention applies to parts made of composite material having woven fiber reinforcement, the weaving being performed using a given weaving scheme throughout the part, or possibly using a plurality of weaving schemes, with the schemes being separated by transition zones. The weaving may be two-dimensional weaving or three-dimensional weaving, which then presents significant advantages in terms of participating in the mechanical strength of the part. A three-dimensional weaving scheme is shown in FIG. 1. The inter-weft distance is marked A therein and the inter-warp distance is marked B.

Regardless of whether it is two- or three-dimensional, the weaving is based on interlacing warp yarns and weft yarns, the warp yarns, which are parallel to one another, crossing the weft yarns, which are likewise parallel to one another. For a given weaving scheme, between two transition zones, the distance between two adjacent warp yarns is substantially constant, and the distance between two adjacent weft yarns is likewise substantially constant. Among other items of geometrical information, these two distances characterize the weaving scheme and also the fatigue or wear state of the part.

Figure 2:
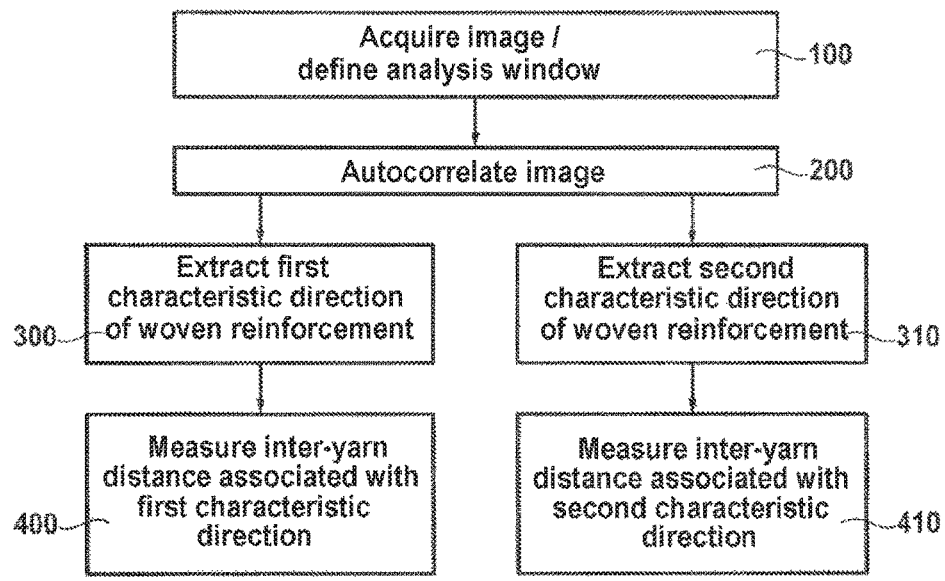
FIG. 2 is a flow chart showing an implementation of the invention.

There follows a description of an implementation of the invention given with reference to FIG. 2 and as applied to such a composite material part, e.g. a part made of a composite material comprising carbon fibers in a carbon matrix.

During a step 100, an image is made of the part by X-ray tomography. It should be recalled that X-ray tomography consists in measuring the attenuation of an X-ray beam passing through the article in different section planes of the article. Thereafter, computer processing can be used on a set of projections to reconstitute a three-dimensional image of the inside of the part. This image may possibly be filtered in order to attenuate artifacts of acquisition and so that the gray level (intensity) allocated to each voxel of 3D image is proportional to the density of material in the part at the point in question.

Once the image has been obtained, it is appropriate to select an analysis window (or observation window) including the zone of the part for which it is desired to discover the fatigue state or characteristics, and in which the weaving scheme is constant (or in other words, in which the weaving is uniform).

During a step 200, autocorrelation is then performed of the 3D image, which is limited to the selected observation window. It should be recalled that the autocorrelation of a signal (regardless of whether the signal is based on a set having one or more dimensions, and of whether it is discrete or continuous) is the cross-correlation of that signal with itself, and the autocorrelation makes it possible to detect regularities, profiles that are repeated in the signal, or a fundamental frequency of the signal, when the signal has one.

Mathematically, the autocorrelation C of a signal $\underline{x}$ is written as follows:

$$C_x(h) = \sum_{n=0}^{N} (x_n - m) - (x_{n-h} - m)$$

where $\underline{m}$ is the mean value of the signal $\underline{x}$ over the window under consideration. The sum is taken over the number N of elements of $\underline{x}$, for a function over a discrete set, and when the function is over a continuous set, the sum is replaced by an integral.

The function is calculated for all the values that can be taken by the value $\underline{h}$, referred to as the autocorrelation interval (or autocorrelation interval vector), in the starting set of the signal.

It should be recalled that the function C has a global maximum for h=0, whatever the signal $\underline{x}$. It is also known that if $\underline{x}$ is periodic, then C is also periodic, with the same period as $\underline{x}$.

In the invention, the value of C is calculated for as large as possible a number of vectors h of the 3D image. This is performed exhaustively by making use of the teaching of the Wiener-Khinchin theorem, which stipulates that the autocorrelation function of a steady stochastic process has a spectral decomposition given by its spectral power density. Thus, the function C may be calculated as follows:

$$C_x = FT^{-1}[|FT(x)|^2]$$

where FT is the Fourier transform and $FT^{-1}$ is the inverse Fourier transform.

Figure 3:
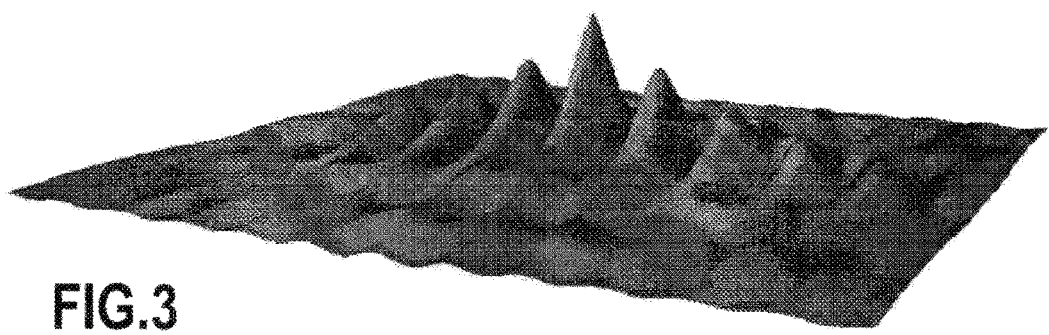
FIG. 3 is a surface rendering of a section of a 3D autocorrelation image of a 3D image of a part made of composite material an autocorrelation image of a 3D image of a composite material part.

By applying this formula to the 3D image in the observation window, it is possible to obtain the set of values taken by the autocorrelation function for all of the vectors included in the image, with computation time that is short. This set is referred to as the (3D) autocorrelation image since it can be viewed as an image, with each vector h being represented by a point x,y,z and being associated with an intensity C, which may for example be displayed in the form of a brightness or a color. The image of the autocorrelation has a plurality of lobes, as can be seen in FIG. 3, which is a surface rendering of a section of a 3D autocorrelation image of a 3D image of a composite material part, the section being taken on a plane passing through the center of the image.

Since the weaving scheme in the observation window is periodic, the autocorrelation has local maxima that can be detected in order to measure the periods of the weaving scheme. This implies initially extracting the two characteristic directions of the woven reinforcement from the autocorrelation value. This is done in steps 300 and 310. It consists in detecting alignments of local maxima in the autocorrelation image, while taking care to search for these alignments in each of the lobes of the image. An alignment must pass through the point h=0.

Once the characteristic directions of the woven reinforcement has been identified, the method continues, for each of these two directions, and independently of each other, by measuring the distance |h| (the norm of the vector h) between two consecutive maxima, and more precisely between the point h=0 and the first local maximum following that point in the characteristic direction identified in the preceding step.

Figure 4:
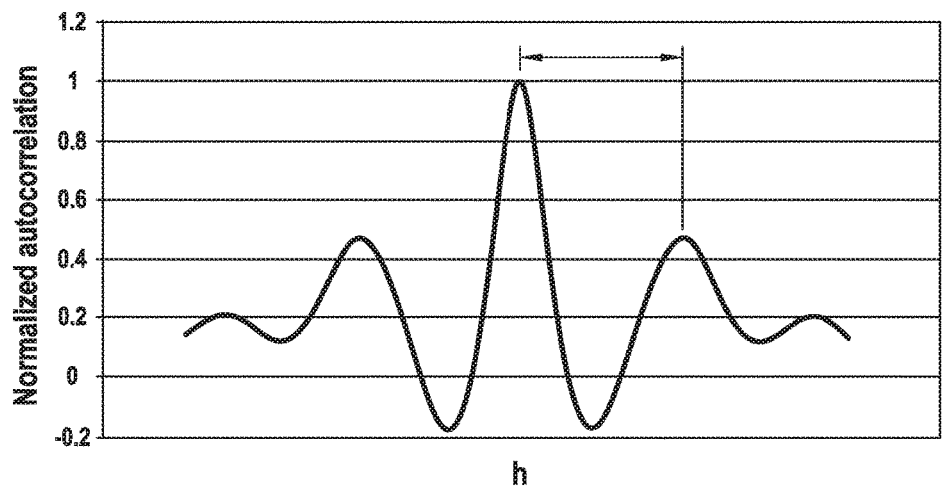
FIGS. 4 and 5 are curves obtained during the final steps of the implementation of FIG. 1.
Figure 5:
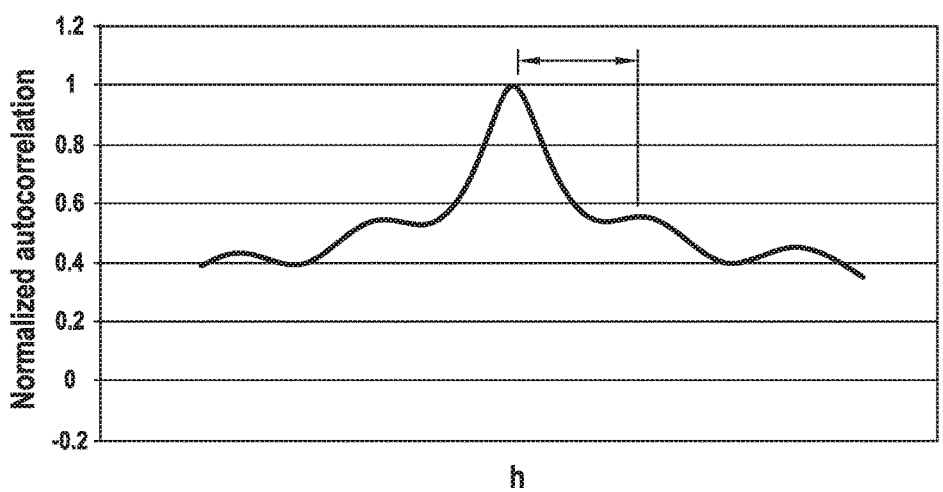

This new step, represented in FIG. 2 by references 400 and 410, is shown in FIGS. 4 and 5, that are curves (1D profile) plotting a value h of the coordinate on the line corresponding to the characteristic direction along the abscissa axis and plotting the autocorrelation value (normalized in this example) of the corresponding point in the autocorrelation image up the ordinate axis.

The value |h| between two consecutive maxima then constitutes the inter-yarn distance in the characteristic direction, which is either the direction of the weft yarns or the direction of the warp yarns. FIG. 4 shows measuring the distance between weft yarns and FIG. 5 shows measuring the distance between warp yarns.

It is possible to distinguish between the weft and warp directions by correlating the autocorrelation result with the initial image and the part.

By way of example, if it is desired to measure the spacing of weft columns situated along the z axis, then it is necessary to look along the z axis in the autocorrelation image in order to be able to measure this spacing. Once measured, this distance is compared with the expected values in order to characterize the part and detect an anomaly, if any.

Figure 6:
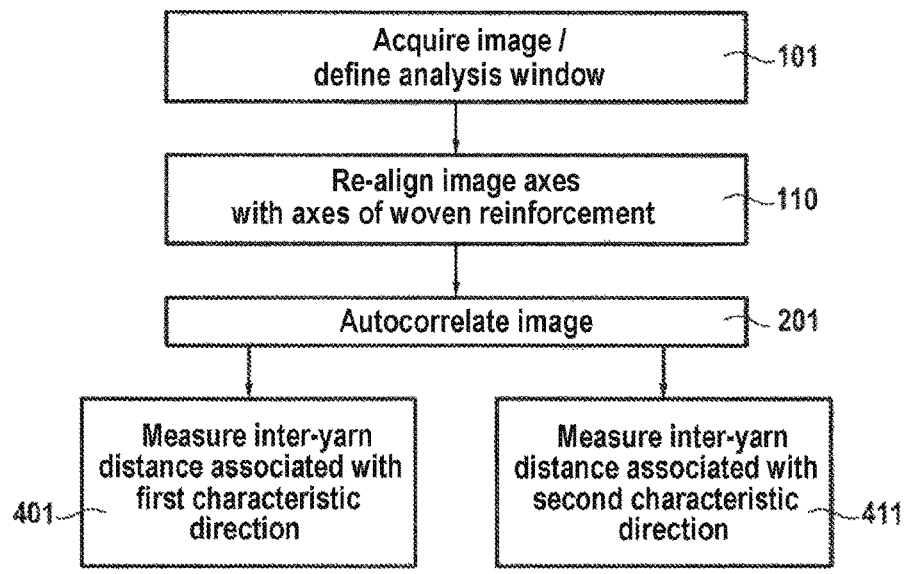
FIG. 6 is a flow chart showing a second implementation of the invention.

FIG. 6 shows a variant of the method. As in the implementation shown in FIG. 2, it involves beginning by a step 101 of acquiring the image and defining an observation window.

This is followed by a step 110 of realigning the axes of the 3D image of the part with the axes of the woven reinforcement, as observed in the image. This makes it possible to take account of variabilities in the weaving, from one part to another, and variabilities in image acquisition from one imaging process to another.

Thereafter, image autocorrelation is performed during step 201. If the realignment is of sufficiently good quality, it is then possible to measure directly the inter-yarn distances in the two characteristic directions identified as being the directions of the image.

It is also possible to combine both realigning the image as mentioned with reference to FIG. 6 and also extracting characteristic directions of the autocorrelation image as mentioned with reference to FIG. 2.

The invention may be performed with parts of any shape, by adapting the observation window to a zone in which the weaving scheme is constant, and then by starting again in a neighboring zone. The dimensions of the observation window may possibly be small in order to cover only a zone in which weaving is uniform. The minimum limiting size is naturally dictated by the inter-yarn distances.

The invention is not limited to a particular implementation, but extends to variants in the context of the ambit of the claims.

The invention claimed is:

1. A method of characterizing a part made of woven composite material, the method comprising: acquiring a three-dimensional image of the part by using a tomography appliance, calculating autocorrelation values of the three-dimensional image in an observation window of the volume of the part for a plurality of spatial vectors used as an autocorrelation interval, and detecting at least one local extremum in the autocorrelation value on a main orientation of the weaving in order to determine a mean in the observation window for a distance between neighboring parallel yarns, wherein the woven composite material is made of a woven fiber reinforcement embedded in a matrix, wherein the method further comprises realigning the image of the part so as to align axes of the image with axes of the woven fiber reinforcement.

2. A characterization method according to claim 1, wherein the autocorrelation values are calculated by using the Wiener-Khinchin theorem.

3. A characterization method according to claim 1, further comprising detecting a main weaving orientation in the plurality of vectors.

4. A characterization method according to claim 1, wherein at least one local extremum is detected for a weft yarn direction and for a warp yarn direction in order to determine means in the observation window respectively for the distances between neighboring weft yarns and between neighboring warp yarns.

5. A characterization method according to claim 1, wherein the part is made of three-dimensionally woven composite material.

6. A characterization method according to claim 1, wherein the part comprises carbon fibers in a carbon matrix.

7. A characterization method according to claim 1, wherein the image is an X-ray tomography image.

8. A characterization method according to claim 1, comprising measuring a distance between two consecutive maxima in the autocorrelation values to determine the distance between neighboring parallel yarns.

* * * * *